US008163308B2

(12) United States Patent
Shah

(10) Patent No.: US 8,163,308 B2
(45) Date of Patent: Apr. 24, 2012

(54) HOMEOPATHY-BASED FORMULATION

(76) Inventor: Rajesh Shah, Mumbai (IN)

( * ) Notice: Subject to any disclaimer, the term of this patent is extended or adjusted under 35 U.S.C. 154(b) by 650 days.

(21) Appl. No.: 12/304,702

(22) PCT Filed: Jun. 25, 2007

(86) PCT No.: PCT/IN2007/000257

§ 371 (c)(1), (2), (4) Date: Dec. 12, 2008

(87) PCT Pub. No.: WO2008/139487

PCT Pub. Date: Nov. 20, 2008

(65) Prior Publication Data

US 2009/0191278 A1 Jul. 30, 2009

(30) Foreign Application Priority Data

May 10, 2007 (IN) ........................... 894/MUM/2007

(51) Int. Cl.
*A61K 35/12* (2006.01)

(52) U.S. Cl. ....................................................... 424/572

(58) Field of Classification Search ......................... None
See application file for complete search history.

(56) References Cited

U.S. PATENT DOCUMENTS 5,603,915 A 2/1997 Nelson et al.

FOREIGN PATENT DOCUMENTS

| | | | |
|---|---|---|---|
| CN | 1456202 | A | 11/2003 |
| EP | 0864323 | A | 9/1998 |
| EP | 0646376 | A | 4/1999 |
| IN | 200400594 | * | 3/2006 |

OTHER PUBLICATIONS

Waisman et al., Arch. Dermatol., 1973, vol. 107, No. 2, Abstract.*
Rutshtein et al., Vesnik Dermatologii I Venerelogii, 1976, vol. 9, p. 63-65.*
Supplementary European Search Report issued Feb. 14, 2011 by the European Patent Office in connection with related European Application No. EP 07 84 9675 (4 pages).

* cited by examiner

*Primary Examiner* — Kade Ariani
(74) *Attorney, Agent, or Firm* — Lucas & Mercanti LLP; Robert P. Michal

(57) ABSTRACT

A formulation comprising a potentized mixture of triturated Lichen planus tissue with histamine in the ratio of about 1:2 to about 2:1 in a vehicle, where the ratio of the mixture to the vehicle, can be varied from 1:99 to 50:50.

8 Claims, No Drawings

HOMEOPATHY-BASED FORMULATION

This application is a 371 of PCT/IN2007/000257 filed Jun. 25, 2007, which in turn claims the priority of 894/MUM/2007 filed May 10, 2007, the priority of both applications is hereby claimed and both applications are incorporated by reference herein.

FIELD OF INVENTION

This invention relates to the field of homeopathy-based formulation.

DEFINITIONS

As used in the present specification, the following words and phrases are generally intended to have the meanings as set forth below, except to the extent that the context in which they are used indicates otherwise.

Potency means capacity of the formulation to produce strong immunological response and/or defense.

Potentization in homeopathy, the process of making a remedy more potent by serial dilution (even to extent that it is unlikely to contain a single molecule of the original substance), powerful strokes is called potentization in the science of homeopathy.

One of the objects of potentization is to reduce all substances designed for therapeutic use to "a state of approximately perfect solution or complete ionization, which is fully accomplished only by infinite dilution." (Arrhenius)

Nosode is a homeopathic preparation made from a diseased or pathological tissues. Substances such as bacteria, virus, hormones, as well as tissue and blood products are used in the fabrication of nosode.

Psoralen ultraviolet A therapy (PUVA) is an acronym for psoralen (a light-sensitizing medication) combined with exposure to ultraviolet light. It is relatively ineffective unless used with a light-sensitizing medication such as psoralen.

Triturate means to rub, crush, grind, or pound into fine particles or a powder; pulverize. A triturated substance means a powdered drug.

Trituration means grinding of powders in a pestle and mortar. It is a process where dissected tissue clumps are broken up by passing them repeatedly by rubbing together in a mortar with a pestle to dissociate the cells. Also in this specification it is the act of reducing a tissue to a fine powder and incorporating it thoroughly with sugar of milk by rubbing the two together in a mortar.

Succussion in Homoeopathy, is a method of potentizing substances conceived by Hahnemann. The substances may be in water/alcohol/mixture of both or in lactose . In general, the alcohol is used in most of the cases, except where drug is only soluble in water. In making liquid attenuations or dilutions, the shaking is necessary with definite proportions of water, alcohol or the mixture of the both, for a set number of times or minutes for preparation of the next higher potency. Hahnemann mentioned to make attenuations by hand process only. Hahnemann himself made the potencies up to 60 centisimal. Succussion means the act or process of shaking violently, especially as a method of diagnosis to detect the presence of fluid and air in a body cavity.

BACKGROUND AND PRIOR ART

Lichen planus (LP) is a common inflammatory, recurrent and chronic disease of the skin and mouth or both. It may also affect the genital mucosa. The name "Lichen" refers to the lichen plant, which grows on rocks or trees and "planus" means flat. The cause of LP is not known. It is not an infectious disease so afflicted person does not transmit it. The disease is not a form of cancer. It does appear to be genetic and it is not related to nutrition. It is considered as an autoimmune disease. Antihypertensice medicines and NSAIDS often induce Lichen Planus. It affects men and women equally.

Reddish-purple, flat-topped lesions that may be very itchy characterize LP of the skin. Some may have a white lacy appearance called Wickham's Striae. It can affect any part of the body, but seems to favor the ventral surface of the wrist and ankles. It also occurs on the lower back, neck and genitals and in rare cases, the scalp and nails. Blisters are rare except in special cases called bullous LP (Vesicles and bullae may occur on typical lesions of LP in this variant due to severe basal cell degeneration induced by the inflammatory process). Although typical appearance of LP makes the disease somewhat easy to identify, a skin biopsy may be needed to confirm the diagnosis. As it heals, dermal LP often leaves a dark brown discoloration on the skin. Like the lesion themselves, these stains may eventually fade with time without treatment.

LP of the mouth most commonly occurs on the inner surface of the cheeks, but can affect the tongue, lips and gums. Oral LP is more difficult to treat and typically lasts longer than LP on the skin. Oral LP typically appears as patches of fine white lines and dots, which usually do not cause problems. More severe from of oral LP can cause painful sores and ulcers in the mouth. Patients with oral LP may be at a slightly increased risk of developing oral cancer. There is no known cure for oral LP although there are many treatments that eliminate the pain of sores. It can lead to poor dental hygiene and gum disease. Careful daily oral hygiene is very important.

LP of the genitals is less common in men than women; women have vulvar or vaginal LP. There may be no problem if it is mild, but red areas or open scores may cause pain, especially with sexual intercourse and needs treatment.

Nail changes have been observed in LP. Nail changes associated with LP include longitudinal ridging and grooving, splitting, nail thinning and nail loss. In severe cases nail may be temporarily or permanently destroyed.

LP can also affect hairy areas such as the scalp in rare cases. This is called lichen planopilaris (also known as Follicular LP). This may accompany typical lesions or may be the sole morphologic type. There are small lesions centered around hair follicles. Lesions on scalp may cause redness, irritation and in some cases, permanent hair loss.

LP may be unpleasant and difficult to treat, but it is a stable condition. The severity and distribution of the disease rarely changes after the first few months.

There is no known cure for LP but symptomatic and ameliorative treatment is often effective in relieving itching and in improving the appearance of the rash until it goes away. Every case of LP is different hence there is no treatment available which is perfect. Two most common treatments include the use of topical corticosteroids or other anti-inflammatory drugs and antihistamines taken orally. More severe cases of LP may require stronger medications such as steroids taken systemically or a specific form of ultraviolet light treatment called PUVA. There are several disadvantages of PUVA treatment:

- It is expensive, needs sophisticated machinery and skilled technicians to handle the machinery.
- Further UV radiation can cause more harm than good and direct exposure to UV rays may result in the formation of skin cancer like Myeloma.

Topical corticosteroids and oral antihistamine medication only suppress the disease and provide relief from pain and itching; it does not cure the disease.

Possible side effects of steroids for males and females include the following:

High blood pressure and heart disease
Liver damage and cancers
Stroke and blood clots
Urinary and bowel problems, such as diarrhea
Headaches, aching joints and muscle cramps
Nausea and vomiting
Sleep problems
Increased risk of ligament and tendon injuries
Severe acne, especially on face and back
Baldness Similarly, the possible side effect of Antihistamine for males and females include the following:

Drowsiness
Dizziness
Loss of appetite
Stomach upset
Vision changes
Dry mouth and nose
Headache U.S. Pat. No. 6,632,836 discloses carbocyclic potassium channel inhibitors. The compounds of this invention are useful in the treatment of autoimmune diseases and infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus.

U.S. Pat. No. 6,437,165 describes invention related to phosphate derivatives as immunoregulatory agents that have immunoregulatory activity. The immunoregulatory abnormalities that can be treated by compounds of this invention can be inflammatory, hyper proliferative skin diseases, psoriasis, atopic dermatitis, contact dermatitis, eczematous dermatitis, seborrhoic dermatitis and Lichen planus.

U.S. Pat. No. 5,763,478 discloses a class of triterpene derivatives, useful as immunosuppressive agents, for the treatment of autoimmune diseases like Lichen planus.

In all these formulations, administration can be oral, topical or parentral. In topical treatment the application of drug is tedious and cumbersome job, it takes time, also availability of the active medication in the body is not predictable. Parentral treatment is painful and it requires skilled person. All the above-mentioned methods of treatment are of allopathic systems of medicines and have its own limitations. The treatment is generally symptomatic and there is no deep level of healing and recovery, also it does not offer long lasting cure and have some side effects.

Hence there is a need for a novel formulation for treatment of chronic inflammatory skin disease such as LP, which has a curative effect rather than a symptomatic effect and has a longer effect. Homeopathy treatment is constitutional; hence there is deep level of healing and recovery. It offers long lasting cure instead of temporary relief and is absolutely harmless, safe and non-toxic.

OBJECTS OF THE INVENTION

One of the objects of the present invention is to provide a medication for allergic skin diseases and other immunologically mediated disorders. Another object of the present invention is to provide a medication, which is free from side effects and is non-toxic.

Yet another object of the present invention is to provide a medication, which is easy to administer.

Yet another object of the present invention is to provide a medication, which is effective and long lasting.

Further object of the present invention is to provide a process for the preparation of the medication, which is economic.

Yet further object of this invention is to provide a process for the preparation of the medication, which is easy to manufacture.

SUMMARY OF THE INVENTION

In accordance with the present invention, there is provided a formulation comprising a potentized mixture of triturated Lichen planus tissue with histamine in the ratio of about 1:2 to about 2:1 in a vehicle, where the mixture to the vehicle, can be varied from 1:99 to 50:50.

Typically, the tissues are collected from a lesion on the body of a patient suffering from Lichen planus.

Typically, the tissues are selected from a group comprising Lichen Planus Pillaris, Nitidus, Lichen Sclerosus Et Atrophic, Lichen Planus Hypertrophicus.

Typically, the tissues include Lichen planus derivatives analogs and all other variants.

Typically, the vehicle is at least one substance selected from a group of solvents consisting of Saccharum Lactis, alcohol and water.

Typically, the potency of the formulation is Ix to 5 million c.

According to this invention there is also provided a process for the preparation of the formulation comprising the following steps:

As per the process in accordance with this invention, pieces of tissue of every variant of Lichen Planus tissue is taken and mixed with Histamine in a ratio of 1 to 10 times. All these pieces were taken in a mortar and about 2 grams Saccharum Lactis is added to it. (Saccharum Lactis is also called as sugar of milk, chemical formula $C_{12}H_{22}O_{11}$, which is an inert substance without having medical properties, used as a vehicle in preparing homeopathic medicines.)

This mixture is triturated for about 20 minutes (6 minutes of grinding, 3 minutes of scraping and 1 min of mixing: this process was repeated twice).

At the end of this the nosode histamine mixture hereinafter designated as LPTNH 1X potency is obtained.

2 mgs of LPTNH 1X is taken and 2 mgs Saccharum Lactis is added to it and the mixture was triturated as above for 20 minutes to obtain LPTNH 2X potency and the procedure is repeated till LPTNH 5X potency is achieved.

Thereafter ½ bottle (of size 1 drachma) is filled with LPTNH 5X and the rest bottle is filled with a solvent such as ethyl alcohol or water and this mixture is given 10 to 20 succussion strokes to obtain LPTNH 6C.

LPTNH 6C is mixed with the solvent in proportion of 50:50 and is given 10 to 20 succussion strokes to obtain LPTNH 7C potency and so on to achieve LPTNH 8C potencies upto 300C and further even upto 5 million C.

Typically, the proportion of homogeneous mixture of Lichen planus and histamine to vehicle is between 1:99 to 50:50.

Typically, the succussion is carried out either manually or by a suitable mechanical device.

Typically, the stroking is carried out either manually or by a suitable mechanical device.

DETAILED DESCRIPTION OF INVENTION

In accordance with the present invention, there is provided a potentized mixture of Lichen planus tissues nosode with histamine.

Lichen Planus is the chronic, inflammatory skin disease causing itching, pain and discomfort to the patient. The disease also has a high incidence of recurrence.

Lichen Planus Tissue Nosode with Histamine (LPTNH) according to this invention falls in the category of homeopathic nosodes, where diseased tissues are used to prepare potentized homeopathic medicine, to treat the diseased conditions related with the source of such medicine. For example, a medicine prepared from the tissues of the cancer of the breast, called carcinosin is used in homeopathy for the case related with cancer. In the present invention, diseased tissues of the skin of a lichen planus patient are used to prepare potentized homeopathic medicines.

For over two centuries, homeopathic practitioners have suggested that serially agitated dilutions of infectious agents (called "nosode") are effective in the prevention of infectious disease.

A 'nosode' is a homeopathic remedy prepared from a pathological specimen. The starting material for preparation of a nosode can be blood, pus, any other body secretion or excretion, or even a diseased fragment of tissue, such as a growth. Rabies nosode, for example, start with the saliva of a rabid dog and is then "potentized".

The preparation of nosodes derives from homotoxicology, a type of homeopathic therapy created by Hans-Heinrich Reckeweg in Germany in the first part of $18^{th}$ century.

Homeopathic medicine, since its inception under Hahnemann at the beginning of the $19^{th}$ century, follows the principle of "infinitesimal." From this notion, the dosages of nosodes are in very minute, diluted and potentized forms. Thus, nosodes are not harmful as the untreated pathological product.

A 'nosode' is comparable to an "oral vaccine" in the sense that its purposes are to "immunize" the body against a specific disease. The major difference between a nosode and a vaccine is of course the extremely small quantity of antigenic material in a nosode.

Nosodes are also used as inter-current remedies in the treatment of chronic diseases. This is the most common use of nosodes in Homeopathic practice.

In accordance with the present invention there is also provided a novel type nosode and comprises preparation of the medication. In this preparation the LP tissues were combined with Histamine were found to be extremely effective for the same. In the present invention, diseased tissues of the skin of a lichen planus patient are used to prepare potentized homeopathic medicines.

Some tissues from the skin of the patient suffering from the lichen planus are collected with aseptic measures and sent to the pathology laboratory for a biopsy study for ascertaining that the tissues are lichen planus positive. (The said tissues of lichen planus include derivatives, analogs and all other variants of lichen planus such as planus pillaris, Lichen nitidus, lichen Sclerosus Et Atrophic, Lichen Planus Hypertrophicus and the like).

Histamine (chemical formula $C_5H_9N_3$) 0.5-5.00 milligrams is mixed with about *1.5-2.5 milligrams of the said tissues of Lichen Planus and then the mixture was mixed with of a suitable vehicle such as Saccharum Lactis.

As per the process in accordance with this invention, pieces of tissue of every variant of Lichen Planus tissue is taken and mixed with Histamine in a ratio of 1 to 10 times. All these pieces were taken in a mortar and about 2 grams Saccharum Lactis is added to it. (Saccharum Lactis is also called as sugar of milk, chemical formula $C_{12}H_{22}O_{11}$, which is an inert substance without having medical properties, used as a vehicle in preparing homeopathic medicines.)

This mixture is triturated for about 20 minutes (6 minutes of grinding, 3 minutes of scraping and 1 min of mixing: this process was repeated twice). At the end of this the nosode histamine mixture hereinafter designated as LPTNH 1X potency is obtained.

2 mgs of LPTNH 1X is taken and 2 grams Saccharum Lactis is added to it and the mixture was triturated as above for 20 minutes to obtain LPTNH 2X potency and the procedure is repeated till LPTNH 5X potency is achieved.

Thereafter ½ bottle (of size 1 drachma) is filled with LPTNH 5X and the rest bottle is filled with a solvent such as ethyl alcohol or water and this mixture is given 10 to 20 succussion strokes to obtain LPTNH 6C.

LPTNH 6C is mixed with the solvent in proportion of 50:50 and is given 10 to 20 succussion strokes to obtain LPTNH 7C potency and so on to achieve LPTNH 8C potencies upto 300C and further even upto 5 million C.

It may be noted that the preparation of Lichen Planus triturated mixture to vehicle such as succrum lactis to the vehicle may be varied from 1:99 to 50:50.

The medication prepared by the present method is administered orally in the form of sugar pills saturated with the potentized Lichen Planus Tissue Nosode with Histamine.

The said preparation of LPTNH triggers immunological stimulus whereby body's own healing mechanism which includes in its orchestra: immunocytes, immunoglobulins, cytokines, T cells, and the like, is put to action; which initiates the healing process in cases of a wide range of autoimmune diseases, inclusive of Lichen Planus.

EXAMPLE

1. As per the process in accordance with this invention, a piece (about two milligram) of every variant of Lichen Planus tissue was taken and mixed with 5 milligram of Histamine. All these pieces were taken in a mortar and about 2 grams Saccharum Lactis was added to it. (Saccharum Lactis is also called as sugar of milk, chemical formula $C_{12}H_{22}O_{11}$, which is an inert substance without having medical properties, used as a vehicle in preparing homeopathic medicines.)

This mixture was triturated for 20 minutes (6 minutes of grinding, 3 minutes of scraping and 1 min of mixing: this process was repeated twice). At the end of this the nosode-histamine mixture hereinafter designated as LPTNH 1X potency was obtained.

2 mgs of LPTNH 1X was taken and 2 grams Saccharum Lactis was added to it and the mixture was triturated as above for 20 minutes to obtain LPTNH 2X potency.

2 mgs of LPTNH 2X was taken and 2 grams Saccharum Lactis was added to it and the mixture was triturated as above for 20 minutes to obtain LPTNH 3X potency.

2 mgs of LPTNH 3X was taken and 2 grams Saccharum Lactis was added to it and the mixture was triturated as above for 20 minutes to obtain LPTNH 4X potency.

2 mgs of LPTNH 4X was taken and 2 grams Saccharum Lactis was added to it and the mixture was triturated as above for 20 minutes to obtain LPTNH 5X potency.

½ bottle (of size 1 drachma) was filled with LPTNH 5X and the rest bottle was filled with ethyl alcohol and this mixture was given 10 succussion strokes to obtain LPTNH 6C.

LPTNH 6C was mixed with ethyl alcohol in proportion of 50:50 and was given 10 succussion strokes to obtain LPTNH 7C potency.

LPTNH 7C was mixed with ethyl alcohol in proportion of 50:50 and was given 10 succussion strokes to obtain LPTNH 8C potency.

LPTNH 8C was mixed with ethyl alcohol in proportion of 50:50 and was given 10 succussion strokes to obtain LPTNH 9C potency.

LPTNH 9C was mixed with ethyl alcohol in proportion of 50:50 and was given 10 succussion strokes to obtain LPTNH 10C potency.

10 drops of LPTNH 10C was mixed with 1 drachma of ethyl alcohol and the mixture was given 10 succussion strokes to obtain LPTNH 11C potency.

10 drops of LPTNH 11C was mixed with 1 drachma of ethyl alcohol and the mixture was given 10 succussion strokes to obtain LPTNH 12C potency.

10 drops of LPTNH 12C was mixed with 1 drachma of ethyl and the mixture was given 10 succussion strokes to obtain LPTNH 13C potency.

The similar process was continued to make further potencies of LPTNH.

Anecdotal Studies:

Provided herein below are some cases studies involving the use of Lichen Planus Tissue Nosode with Histamine in accordance with this invention:

Case 1.

A 45 years old presented with Lichen Planus almost all over the body. The patient was suffering since 10 years. She was prescribed local steroid application as well as oral steroids, which led to the development of diabetes. However, the Lichen Planus improved for a short time and then it resurfaced; now resistant to local steroids. It was an obstinate case of Lichen Planus.

She was prescribed LPTNH 30c potency, to be taken twice a day for one month. The skin lesions improved and the itching reduced. The medicine then was continued for next three months. There was further improvement. Oral steroids were slowly reduced and stopped. Local steroid application was restricted to use only if the lesions become extremely itchy. After three months, local application of steroids was also stopped. The extent of Lichen Planus on her body reduced by over 80% and was almost non-itchy. The medicine was continued in 100c potency for three more months, which led to almost 100% cure.

Case 2.

A male aged 25 years was affected with Lichen Planus on legs for 8 months. The lesions were multiple, with intense itching and bleeding. The patient had used local steroid formulations for one month with little relief.

He was prescribed LPTNH 30c, three times a day for one month, which reduced his itching as well as the skin lesions. Local steroid application was stopped. LPTNH 200c was prescribed for two more months. Lichen Planus cleared completely.

Case 3.

A 54 years old gentleman presented with a history of Lichen Planus on wrist, back and abdomen since about three months. He had not taken any medication till he consulted the inventor. He was prescribed LPTNH 30c, three times a day and was reviewed after six weeks, where he reported over 80% improvement. The medicine was continued for two more months and the skin lesions vanished totally. The treatment was concluded.

Case 4.

A young girl aged 10 years approached with history of Lichen Planus on legs and back, since three years. She was prescribed LPTNH 30c, three times a day for two months. She reported about 50% improvement in two months. The treatment was continued with LPTNH 200c potency for next four months, to achieve 80% improvement. Further, LPTNH 300c was prescribed for two more months with some more improvement. Then she was prescribed LPTNH 500c for next two months and she was almost 100% cured.

Case 5.

A female aged 38 years presented with a history of dermal and oral Lichen Planus since about 15 years, with temporary improvement whenever she was administered oral and local steroids. She developed many adverse effects due to steroids and she decided to discontinue with it.

Patient was prescribed LPTNH 30c, three times a day for six weeks. Some improvement was observed. She was put on LPTNH 300c, thrice a day for next six weeks and she responded to over 50%. LPTNH 300c, LPTNH 400c, LPTNH 500c was subsequently prescribed for next eight weeks each to achieve about 80% cure in skin lesions and about 60% improvement in oral lesions. LPTNH 1000c was prescribed once a day for next ten weeks and she was further improved up to 90% (skin lesions) and over 80% in oral lesions. Patient did not come to follow up thereafter.

Case 6.

A male aged 62 years presented with a history of oral Lichen Planus since about five years. He was prescribed LPTNH 30c, thrice a day for six weeks. He was then prescribed LPTNH 100c, thrice a day for next eight weeks, to achieve 30% improvement. He was prescribed LPTNH 500c, twice a day to achieve about 60% improvement. Subsequently, he was prescribed LPTNH 800c, LPTNH 1000c for next 8 weeks. He was almost free from oral lesions of Lichen Planus.

Case 7.

A female aged 69 years presented with a history of obstinate case of Lichen Planus, which had affected her skin, oral mucosa as well as her vagina. She tried all possible modes of steroids such as oral steroid mouthwash, steroid injections and vaginal steroid application; but she only gets short lasting relief from painful blisters in mouth and vagina.

She was prescribed LPTNH 200c, three times a day for six weeks. She was then administered LPTNH 300c, thrice a day for ten weeks. She was better with regards to skin and oral lesions; but her vaginal lesions did not improve. She was prescribed LPTNH 1000c, three times a day for six weeks. She reported over all improvement of about 60% in oral, dermal and vaginal lesions. The medicine was continued for eight more weeks, she was improved by 70 to 80%.

Case 8.

A male aged 58 years presented with a history of oral Lichen Planus since about four years. He had not taken any form of steroids but only local analgesic gel to relieve from pain. He was prescribed LPTNH 50c, thrice a day for a month. He was 30% better. The medicine was continued in 100c potency for next 8 weeks and he was improved further to 60%. He was then prescribed LPTNH 200c for 8 weeks and LPTNH 500c for next 8 weeks. He was almost 85 to 90% cured.

Case 9.

A male aged 56 years approached with history of multiple skin lesions of Lichen Planus on his legs and hands, since eight years. He was prescribed LPTNH 30c, thrice a day for eight weeks. He improved by 70%. He was then prescribed LPTNH 200c, thrice a day for next ten weeks. His lesions improved almost 90%.

Case 10.

A 28 years old gentleman presented with a history of dermal Lichen Planus on hands, legs, abdomen, back and chest since about six months, following antimalarial medicines. He was prescribed LPTNH 30c, thrice a day for six weeks; he improved by about 30%. He was then prescribed LPTNH 200c, thrice a day for next eight weeks and improved by over 90%. He was then prescribed LPTNH 1000c, once a day for a month; the lesions disappeared completely.

Case 11.

A young boy aged 12 years, reported with extensive Lichen Planus since three years, affecting his limbs, back and abdomen. He had had treatment with local steroids for some time with little relief. He was prescribed LPTNH 50c, twice a day for six weeks. He reported improvement up to 50%. The Medicine was continued for another two months to reach 70% improvement. The potency was raised up to LPTNH 300c, twice a day for ten weeks and he improved by over 90%. The treatment was continued for two more months and then concluded as he recovered almost completely.

Case 12.

A 37 years old patient, presented with a history of Lichen Planus affecting his skin on legs and oral mucosa since about five years. He was prescribed LPTNH 50c, thrice a day for two months; whereby he improved over 70%. The medicine was administered in 100c potency, twice a day for next three months and his lesions vanished almost completely.

Case 13.

A female aged 44 years presented with a history of Lichen Planus on scalp, skin and nails since about 15 years. She was prescribed LPTNH 30c for six weeks, without any relief, she was then prescribed LPTNH 300c, twice a day for six week and her skin lesions were considerably better. She was then prescribed LPTNH 500c, twice a day for next eight weeks. Her skin lesions improved further, nails improved to some extent. However, her scalp did not improve much as there was more of scarring and fibrosis.

Case 14.

A 46 year old gentleman presented with a history of Lichen Planus on legs since about three months. He had not taken any treatment and was prescribed LPTNH 50c, thrice a day for a month. He improved by over 60%. The medicines were repeated in 100c potency, twice a day for next six weeks. His Lichen Planus disappeared completely.

Case 15.

A female aged 52 years approached with history of Lichen Planus on legs, back, hands and mouth since 20 years. She had tried the conventional treatment for Lichen Planus but only with temporary relief. She was put on LPTNH 50c; thrice a day for six weeks and improved by about 20%. She was then prescribed LPTNH 300c, twice a day for next eight weeks to achieve 50% improvement on most lesions. She discontinued the treatment for about one year, as circumstances did not permit to continue. She reported once again after one year with most lesions as observed during the last visit. She was prescribed LPTNH 500c, twice a day and she was better by about 70% in next three months. The medicine was prescribed in LPTNH 500c, 1000c, and 2000c for next about eight months and the patient was almost cured.

While considerable emphasis has been placed herein on the specific structure of the preferred embodiment, it will be appreciated that many alterations can be made and that many modifications can be made in the preferred embodiment without departing from the principles of the invention. These and other changes in the preferred embodiment as well as other embodiments of the invention will be apparent to those skilled in the art from the disclosure herein, whereby it is to be distinctly understood that the foregoing descriptive matter is to be interpreted merely as illustrative of the invention and not as a limitation

The invention claimed is:

1. An oral formulation for treating a patient suffering from Lichen planus comprising a potentized mixture of triturated Lichen planus tissue with histamine in the ratio of about 1:2 to about 2:1 in a vehicle, where the ratio of the mixture to the vehicle, ranges between 1:99 and 50:50, wherein the tissues is selected from the group consisting of Lichen Planus Pillaris, Nitidus, Lichen Sclerosus Et Atrophic, Lichen Planus Hypertrophicus, and Lichen planus.

2. The formulation as claimed in claim 1, wherein, the tissue is collected from a lesion on the body of a patient suffering from Lichen planus.

3. The formulation as claimed in claim 1, wherein, the vehicle is at least one substance selected from a group of substances consisting of Saccharum Lactis, alcohol and water.

4. The formulation as claimed in claim 1, wherein, the potency of the formulation is 1x to 5 million c.

5. The formulation as claimed in claim 1, wherein said formulation is prepared by the following steps:

(a) mixing together pieces of the Lichen Planus tissue with Histamine in a ratio of 1 to 10 times to form a mixture;

(b) triturating the mixture with the vehicle in a mixture to vehicle ratio of about 1:99 to about 50:50 to obtain triturated mixture designated as LPTNH 1X potency;

(c) triturating a predetermined quantity of LPTNH 1X potency with predetermined quantity of the vehicle to obtain LPTNH 2X potency till LPTNH 5X potency; and (d) successing a predetermined quantity of LPTNH 5X potency with predetermined quantity of the vehicle to obtain LPTNH 6c potency till LPTNH 5 million c potency.

6. The process for making a formulation as claimed in claim 5, wherein the vehicle is a vehicle selected from Saccharum Lactis, alcohol and water.

7. The process for making a formulation as claimed in claim 5, wherein the trituration steps are carried out for about 20 minutes (6 minutes of grinding, 3 minutes of scraping and 1 min of mixing) and being repeated at least twice.

8. The process for making a formulation as claimed in claim 5, wherein the step of successing is carried out by mechanical striking a container containing a mixture with 10 to 20 strokes.

* * * * *